US008188152B2

(12) United States Patent
Bannister et al.

(10) Patent No.: US 8,188,152 B2
(45) Date of Patent: *May 29, 2012

(54) 2-AMINOALCOHOLS FOR THE TREATMENT OF NEURODEGENERATIVE DISEASES

(75) Inventors: Robin Mark Bannister, Saffron Walden (GB); Michael Harvey Lyne, Saffron Walden (GB)

(73) Assignee: Biocopea Limited (GB)

( * ) Notice: Subject to any disclaimer, the term of this patent is extended or adjusted under 35 U.S.C. 154(b) by 870 days.

This patent is subject to a terminal disclaimer.

(21) Appl. No.: 12/066,904

(22) PCT Filed: Sep. 21, 2006

(86) PCT No.: PCT/GB2006/003529
§ 371 (c)(1),
(2), (4) Date: Sep. 8, 2008

(87) PCT Pub. No.: WO2007/034200
PCT Pub. Date: Mar. 29, 2007

(65) Prior Publication Data
US 2009/0192229 A1    Jul. 30, 2009

(30) Foreign Application Priority Data
Sep. 21, 2005 (GB) .................................. 0519274.5

(51) Int. Cl.
*A01N 27/00* (2006.01)
(52) U.S. Cl. ........................................ 514/764; 514/903
(58) Field of Classification Search .................. 514/764, 514/903
See application file for complete search history.

(56) References Cited

U.S. PATENT DOCUMENTS 5,264,459 A * 11/1993 Chelmicka-Schorr et al. ............................ 514/646
2004/0002546 A1    1/2004 Altschuler
2006/0252788 A1 * 11/2006 Went et al. ..................... 514/294

FOREIGN PATENT DOCUMENTS

| EP | 1 300 405 A1 | 4/2003 |
|---|---|---|
| WO | WO 00/51546 A2 | 9/2000 |
| WO | WO 01/62257 A2 | 8/2001 |
| WO | WO 2005/044248 A1 | 5/2005 |
| WO | WO 2005/089741 A2 | 9/2005 |

OTHER PUBLICATIONS

Wiegmann et al. B-adrenergic agonists suppress chronic/relapsing experimental allergic encephalomyelitis (CREAE) in Lewis rats. Journal of Neuroimmunology 56 (1995) 201-206.*
Duffy, J.D. and Campbell, J. "Bupropion for the treatment of fatigue associated with multiple sclerosis" *Psychosomatics*, 1994, pp. 170-171, vol. 35, No. 2.

* cited by examiner

*Primary Examiner* — Sreeni Padmanabhan
*Assistant Examiner* — Renee Claytor
(74) *Attorney, Agent, or Firm* — Peter D. Weinstein

(57) ABSTRACT

Use of a compound for the manufacture of a medicament for use in therapy of a neurodegenerative condition, wherein the compound is of formula (I): wherein $R_1$ is $CHR_4$—$OR_5$ or $CHR_4$—$SR_5$, or aryl or heteroaryi optionally substituted with one or more groups $R_6$; $R_2$ is alkyl or is part of a ring with $R_3$; $R_3$ is H, alkyl or $CH_2$ (when forming part of a ring with $R_2$); $R_4$ is H or alkyl or is part of a ring with $R_5$; $R_5$ is aryl or heteroaryi optionally substituted with $R_7$; each $R_6$ is independently alkyl, $CF_3$, OH, Oalkyl, OCOalkyl, $CONH_2$, CN, halogen, $NH_2$, $NO_2$, NHCHO, $NHCONH_2$, $NHSO_2$alkyl, $CONH_2$, SOMe, $SO_2NH_2$, Salkyl, $CH_2SO_2$alkyl or OCONalkyl$_2$; $R_7$ is $R_8$ or $(CH_2)_nOR_8$, $R_9$, $CF_3$, OH, $OR_9$, $OCOR_9$, $COR_9$, $COOR_9$, $CONH_2$, $CH_2CONH_2$, CN, halogen, $NH_2$, $NO_2$, NHCHO, $NHCONH_2$, $NHCONHR_7$, $NHCON(R_9)_2$, $NHCOR_9$, NHCOaryl, $NHSO_2$Me, $CONH_2$, SMe, SOMe or $SO_2NH_2$; $R_8$ is $(CH_2)_nOR_9$, $(CH)_nOR_9$, $(CH_2)_nCOOR_9$ or $(CH_2)_nCOaryl$; $R_9$ is alkyl or cycloalkyl; and n is 1 to 4; or a salt thereof.

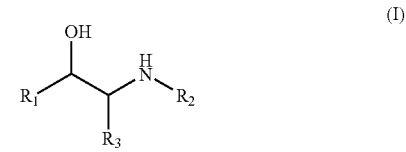

(I)

4 Claims, 1 Drawing Sheet

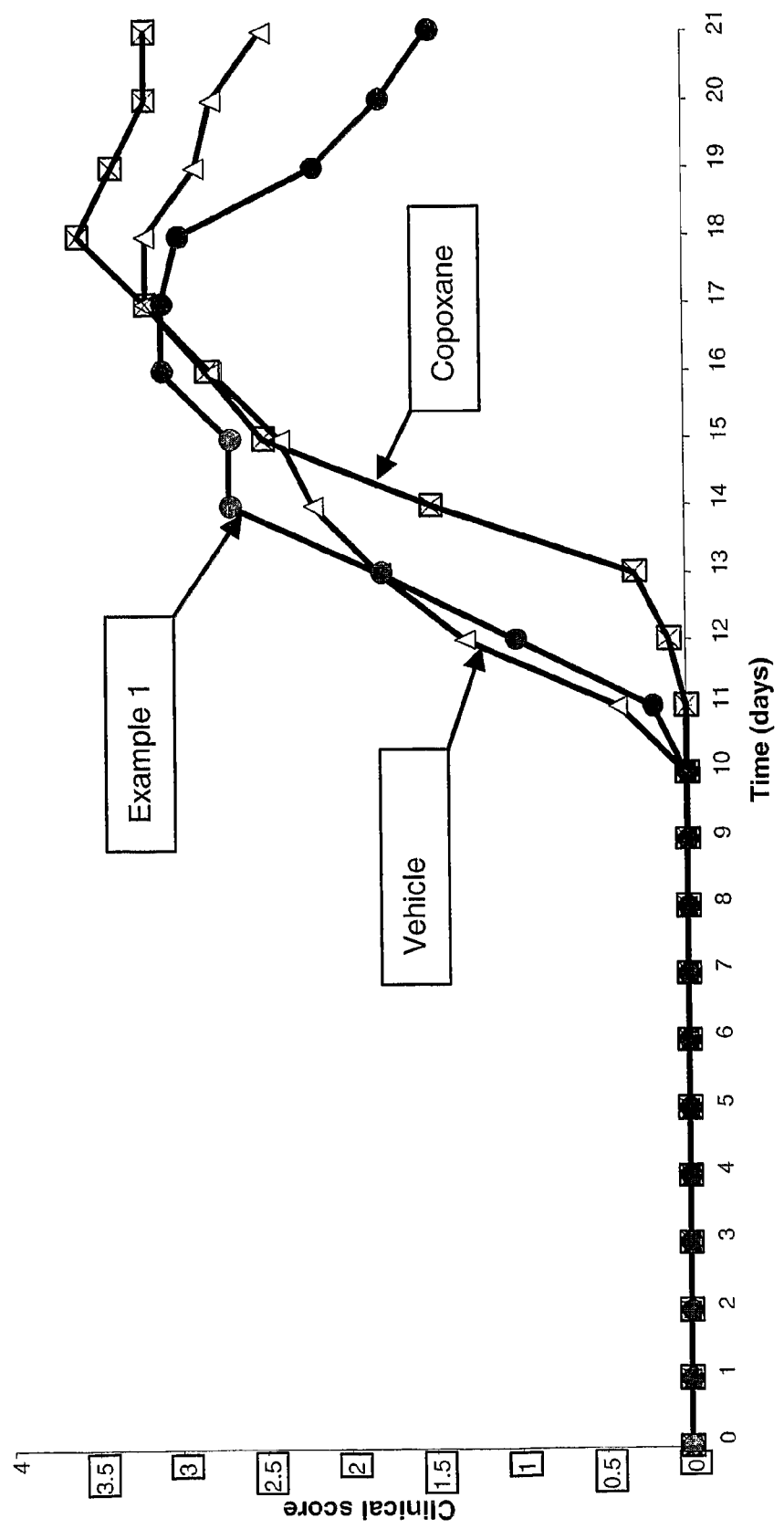

2-AMINOALCOHOLS FOR THE TREATMENT OF NEURODEGENERATIVE DISEASES

This application is a National Stage Application of International Application Number PCT/GB2006/003529, filed Sep. 21, 2006, which claims priority to Great Britain Application No. 0519274.5, filed Sep. 21, 2005, all of which are incorporated herein in their entirety.

FIELD OF THE INVENTION

This invention relates to the treatment of neurodegenerative diseases.

BACKGROUND OF THE INVENTION

Neurodegenerative diseases are conditions that affect brain or peripheral nerve function. They result from the deterioration of neurons and they are characterised by progressive central or peripheral nervous dysfunction. They are divided into two groups: conditions causing problems with movement or sensation and conditions affecting memory or related to dementia. Neurodegenerative diseases include: Alexander disease, Alper's disease, Alzheimer's disease, amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, Parkinson's disease, Pelizaeus-Merzbacher disease, Pick's disease, primary lateral sclerosis, Refsum's disease, Sandhoff disease, Schilder's disease, Steele-Richardson-Olszewski disease, tabes dorsalis and Guillain-Barre Syndrome. Currently there are no effective cures for these conditions, and very few treatments are available.

SUMMARY OF THE INVENTION

Surprisingly, it has been found that beta-amino alcohols are useful for the treatment of neurodegenerative diseases. The beta-amino alcohols are of formula (I)

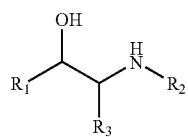
(I)

wherein
$R_1$ is $CHR_4$—$OR_5$ or $CHR_4$—$SR_5$, or aryl or heteroaryl optionally substituted with one or more groups $R_6$;
$R_2$ is alkyl or is part of a ring with $R_3$;
$R_3$ is H, alkyl or $CH_2$ (when forming part of a ring with $R_2$);
$R_4$ is H or alkyl or is part of a ring with $R_5$;
$R_5$ is aryl or heteroaryl optionally substituted with $R_7$;
each $R_6$ is independently alkyl, $CF_3$, OH, Oalkyl, OCOalkyl, $CONH_2$, CN, halogen, $NH_2$, $NO_2$, NHCHO, $NHCONH_2$, $NHSO_2$alkyl, $CONH_2$, SOMe, $SO_2NH_2$, Salkyl, $CH_2SO_2$alkyl or $OCONalkyl_2$;
$R_7$ is $R_8$ or $(CH_2)_nOR_8$, $R_9$, $CF_3$, OH, $OR_9$, $OCOR_9$, $COR_9$, $COOR_9$, $CONH_2$, $CH_2CONH_2$, CN, halogen, $NH_2$, $NO_2$, NHCHO, $NHCONH_2$, $NHCONHR_7$, $NHCON(R_9)_2$, $NHCOR_9$, NHCOaryl, $NHSO_2Me$, $CONH_2$, SMe, SOMe or $SO_2NH_2$;
$R_8$ is $(CH_2)_nOR_9$, $(CH)_nOR_9$, $(CH_2)_nCOOR_9$ or $(CH_2)_n$COaryl;
$R_9$ is alkyl or cycloalkyl; and
n is 1 to 4;
or a salt thereof.

DESCRIPTION OF THE DRAWING

FIG. 1 is a graph showing the effects of (+)-erythro-2-tert-butylamino-1-(3-chlorophenyl)-propan-1-ol hydrochloride (Example 1) and copaxone on neurological scores induced in a model.

DESCRIPTION OF THE INVENTION

It is understood that the invention refers to salts, e.g. the hydrochloride, metabolites and pro-drugs thereof, as well as any diastereomers and enantiomers of (I).

Some of the compounds of formula (I) have antihypertensive, vasodilator, sympathomimetic, bronchodilator or cardiostimulant activity through agonism and antagonism at alpha and beta adrenoceptors. These agents have at least one chiral centre and their activity at the alpha or beta adrenoceptors resides mainly or solely in one of the enantiomers. If the molecule has more than one chiral centre, the activity at the alpha or beta adrenoceptors resides mainly in one of the diastereomers.

The preferred diastereomer or enantiomer of (I) has little or no activity at the α or β adrenoceptors. This activity may be determined by use of the appropriate in vitro assay.

The compounds of formula (I) according to the invention are useful to treat neurodegenerative diseases including Alexander disease, Alper's disease, Alzheimer's disease, amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, Parkinson's disease, Pelizaeus-Merzbacher disease, Pick's disease, primary lateral sclerosis, Refsum's disease, Sandhoff disease, Schilder's disease, Steele-Richardson-Olszewski disease, tabes dorsalis or Guillain-Barre Syndrome.

Compounds of formula (I) may be used according to the invention alone, in combination with another therapeutic agent, or in treatment of a patient also being administered another therapeutic agent. Such other agents include cholinesterase inhibitors (examples including galantamine, rivastigmine, donepezil, tacrine), steroids, interferons and glutamate receptor agents such as AMPA, kainate agents and NMDA antagonists (examples including memantine).

Any suitable route of administration can be used. For example, any of oral, topical, parenteral, intracerebroventricular, spinal, ocular, rectal, vaginal, inhalation, buccal, sublingual and intranasal delivery routes may be suitable. The dose of the active agent will depend on the nature and degree of the condition, the age and condition of the patient and other factors known to those skilled in the art. A typical dose is 0.1-100 mg given one to three times per day.

The following Example illustrates the invention.

EXAMPLE

Experimental Allergic Encephalomyelitis (EAE) is a central nervous system, autoimmune, demyleinating disease, that mimics many aspects of multiple sclerosis. Acute models of murine EAE are often utilised to evaluate the efficacy of therapeutics.

Method

Acclimatised SJL mice were sensitised by a subcutaneous injection proteolipid protein (PLP) in Freund's complete adjuvant (CFA) acting as an encephalitogenic inoculum. Innoculum was administered subcutaneously at a concentration of 125 μg PLP/300 μg CFA in a volume of 200 μl. 48 hours later, an intraperitoneal injection of pertussis toxin (PTX) was administered at a dose of 20 μg/kg, to increase blood-brain barrier permeability.

(+)-Erythro-2-tert-butylamino-1-(3-chlorophenyl)-propan-1-ol hydrochloride and copoxane were administered from the first day of the experiment and once a day until the end. (+)-Erythro-2-tert-butylamino-1-(3-chlorophenyl)-propan-1-ol hydrochloride was administered orally at a dose of 10 mg/kg. Copaxone was administered intraperitoneally at a dose of 25 mg/kg. Throughout the experiment, careful clinical examinations and body weights were taken to observe the well being of the animal. In addition, clinical scoring of the EAE symptoms was taken to the classical 0-5 scale, as follows:

0 Normal reactions
1 Tail weakness
2 Hind leg weakness and paresis
3 Hind leg paralysis
4 Quadriplegia
5 Moribund/death Results FIG. 1 describes the effect of orally administered (+)-erythro-2-tert-butylamino-1-(3-chlorophenyl)-propan-1-ol hydrochloride (10 mg/kg) and intraperitoneally administered copoxone (25 mg/kg) versus the vehicle control (for (+)-erythro-2-tert-butylamino-1-(3-chlorophenyl)-propan-1-ol hydrochloride) on SJL mouse EAE neurological scores.

EAE-induced mice exhibited pronounced neurological deficits as defined by the vehicle group. Weaknesses in hind limb were recorded by day 10 and peaked at day 17 with a maximum neurological deficits score of 2; which relates to deficits in walking and unsteady gait.

(+)-Erythro-2-tert-butylamino-1-(3-chlorophenyl)-propan-1-ol hydrochloride showed no improvement in the maximal neurologic score, but exhibited a more rapid improvement in symptoms, accelerating disease resolution compared to the vehicle.

Copaxone delayed the onset of neurological symptoms by 2-3 days, but had no effect on the improvement of symptoms, seemingly worsening this aspect of the model.

These data show that (+)-erythro-2-tert-butylamino-1-(3-chlorophenyl)-propan-1-ol hydrochloride has a quantifiable effect on the SJL EAE model of multiple sclerosis, and suggesting that this molecule is a potential treatment for multiple sclerosis.

The invention claimed is:

1. A method for providing therapy for a neurodegenerative condition, wherein said method comprises administering, to a patient in need of such therapy, a compound that is (+)-erythro-2-tert-butylamino-1-(3-chlorophenyl)-propan-1-ol or a salt thereof; wherein the compound has little or no activity at an α or β adrenoceptor; and wherein the condition for which therapy is provided is multiple sclerosis.

2. The method according to claim 1, wherein the patient is also administered another therapeutic agent selected from cholinesterase inhibitors, steroids, interferons and glutamate receptor agents.

3. The method according to claim 2, wherein compound (I) and said another agent are provided in combination.

4. The method, according to claim 2, wherein said glutamate receptor agent is selected from, AMPA, kappa agents and NMDA antagonists.

* * * * *